(12) United States Patent
Kataoka et al.

(10) Patent No.: US 6,172,224 B1
(45) Date of Patent: Jan. 9, 2001

(54) PROCESS FOR ISOLATING 2-AMINO-6-CHLORO-9-[(1'S,2'R)-1'2'-BIS (HYDROXYMETHYL)-CYCLOPROPANE-1'-YL]METHYLPURINE AND AN OPTICAL ISOMER THEREOF

(75) Inventors: Noriyasu Kataoka; Toshihiro Matsuzawa; Masanobu Yatagai, all of Kawasaki (JP)

(73) Assignee: Ajinomoto Co., Inc., Tokyo (JP)

( * ) Notice: Under 35 U.S.C. 154(b), the term of this patent shall be extended for 0 days.

(21) Appl. No.: 09/263,999

(22) Filed: Mar. 8, 1999

(30) Foreign Application Priority Data

Mar. 9, 1998 (JP) .................................. 10-056756

(51) Int. Cl.$^7$ ................................. C07D 473/32
(52) U.S. Cl. ............................................. 544/277
(58) Field of Search ............................... 544/277

(56) References Cited

U.S. PATENT DOCUMENTS 5,925,765 * 7/1999 Onishi et al. .................... 544/264

FOREIGN PATENT DOCUMENTS

| 0 502 690 | 9/1992 | (EP) . |
|---|---|---|
| 0 675 123 | 10/1995 | (EP) . |
| 0 890 574 | 1/1999 | (EP) . |
| 5-78357 | 3/1993 | (JP) . |
| 6-80670 | 3/1994 | (JP) . |
| 6-227982 | 8/1994 | (JP) . |
| 7-316155 | 12/1995 | (JP) . |
| 08041035 | * 2/1996 | (JP) . |

OTHER PUBLICATIONS

T. Sekiyama et al, J. Med. Chem., 41, 1998, 1284–1298.*

* cited by examiner

Primary Examiner—Mark L. Berch
Assistant Examiner—Thomas McKenzie
(74) Attorney, Agent, or Firm—Oblon, Spivak, McClelland, Maier & Neustadt, P.C.

(57) ABSTRACT

A process for purifying 2-amino-6-chloro-9-[(1'S,2'R)-1',2'-bis(hydroxymethyl) cycdopropane-1'-yl]methylpurine represented by the following formula (5) comprises the step of selectively isolating 2-amino-6-chloro-9-[(1'S,2'R)-1',2'-bis(hydroxymethyl) cyclopropane-1'-yl]methylpurine from a mixture of 2-amino-6-chloro-9-[(1'S,2'R)-1',2'-bis(hydroxymethyl)cyclopropane-1'-yl]methylpurine and 2-amino-6-chloro-7-[(1'S,2'R)-1',2'-bis(hydroxymethyl) cyclopropane-1'-yl]methylpurine represented by the following formula (6) by the crystallization. This process has a satisfactory medicinal quality on an industrial scale without necessitating complicated operations such as chromatographic purification.

10 Claims, No Drawings

PROCESS FOR ISOLATING 2-AMINO-6-CHLORO-9-[(1'S,2'R)-1'2'-BIS (HYDROXYMETHYL)-CYCLOPROPANE-1'-YL]METHYLPURINE AND AN OPTICAL ISOMER THEREOF

BACKGROUND OF THE INVENTION

The present invention relates to a process for preparing nucleoside acid derivatives useful as antiviral agents. In particular, the invention relates to a process for preparing nucleoside derivatives by alkylating purine bases.

It is known that 2-amino-9-[(1'S,2'R)-1',2'-bis (hydroxymethyl)cyclopropane-1'-yl]methylpurine represented by the following formula (1) and 9-[(1'S,2'R)-1',2'-bis(hydroxymethyl)cyclopropane-1'-yl]methylguanine represented by the following formula (2) have a strong antiviral activity [Japanese Patent Unexamined Published Application (hereinafter referred to as "J. P. KOKAI") Nos. Hei 5-78357 and Hei 6-227982].

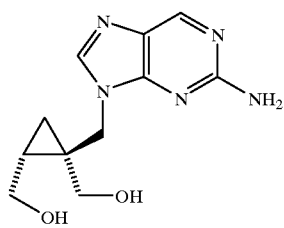

(1)

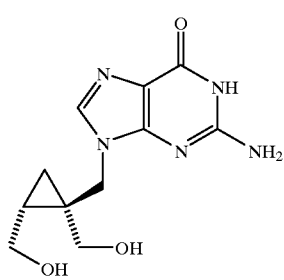

(2)

It is also known that the compounds of the above formulae (1) and (2) are produced by alkylating protected purine bases to obtain corresponding purine bases alkylated at the N-7 position and N-9 position and purifying them by silica gel column chromatography and removing the protecting group (J. P. KOKAI Nos. Hei 6-80670 and Hei 7-316155.

It is generally known that in the preparation of the antiviral agents by the condensation reaction of a purine base and an alkylating agent, the alkylation reaction occurs at both N-7 position and N-9 position of the purine base as described above. Since the intended compound is usually the purine base substituted at the N-9 position, conventionally it was inevitable to isolate it by the column chromatography.

SUMMARY OF THE INVENTION

The object of the present invention is to provide a process for preparing antiviral agents of the above general formulae (1) and (2) having a satisfactory medicinal quality on an industrial scale without necessitating complicated operations such as chromatographic purification.

This and other objects of the present invention will be apparent from the following description and Examples.

After intensive investigations made for the purpose of solving the above-described problems, the inventors have found that an intended compound (5) substituted at the N-9 position and having a high purity can be obtained in the preparation of 2-amino-9-[(1'S, 2'R)-1',2'-bis (hydroxymethyl)cyclopropane-1'-yl] methylpurine (1) or 2-amino-9-[(1'S, 2R)-1',2'-bis(hydroxymethyl) cyclopropane-1'-yl] methylguanine (2), by condensing 2-amino-6-chloropurine (as a purine base) with a compound, obtained by substituting hydroxyl group of (3-oxa-2-oxobicyclo [3.1.0]hexane-1-yl)methanol (as an alkylating agent) with a leaving group, to obtain 2-amino-6-chloro-9-[(1'S,2'R)-1',2'-bis(hydroxymethyl)cyclopropane-1'-yl] methylpurine represented by the following formula (3) and an isomer thereof at the N-7 position, i.e. 2-amino-6-chloro-7-[(1'S,2'R)-1',2'-bis(hydroxymethyl)cyclopropane-1'-yl] methylpurine represented by the following formula (4) which is a by-product, and without separating them from each other by the silica gel column chromatography, subjecting a mixture of 2-amino-6-chloro-9-[(1'S,2'R)-1',2'-bis (hydroxymethyl) cyclopropane-1'-yl]methylpurine represented by the following formula (5) and 2-amino-6-chloro-7-[(1'S,2'R)-1',2'-bis(hydroxymethyl)cyclopropane-1'-yl] methylpurine represented by the following formula (6) obtained by reducing the lactone parts of the compounds represented by the following formulae (3) and (4) to the crystallization from water or isopropanol to precipitate only the intended isomer at the N-9 position in the form of crystals, and isolating it. The inventors have also found that the obtained compound can be subjected to the hydrogenolysis to obtain a compound of formula (1) or chlorine group at the 6-position of the nucleic acid base can be hydrolyzed to obtain a compound of formula (2). The present invention has been completed on the basis of these findings.

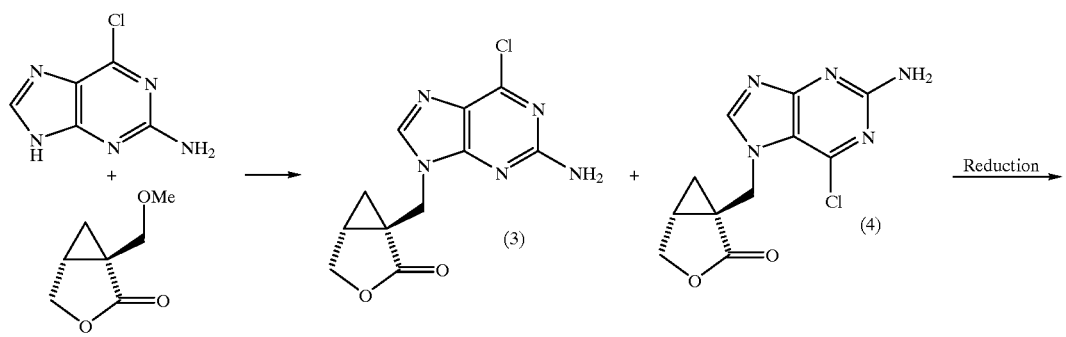

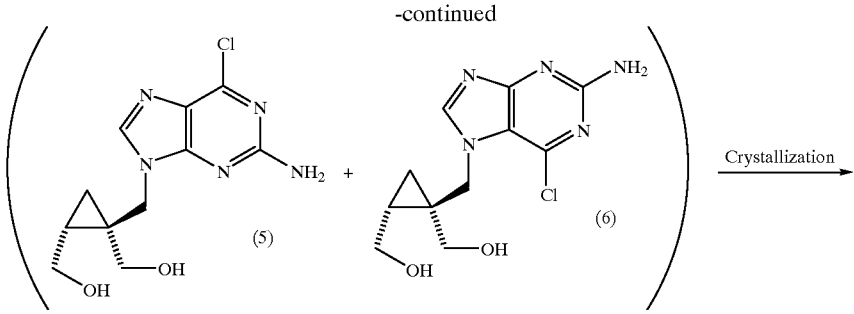

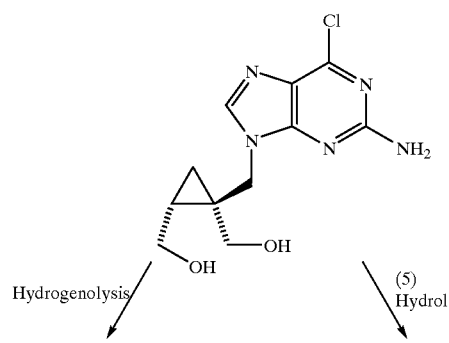

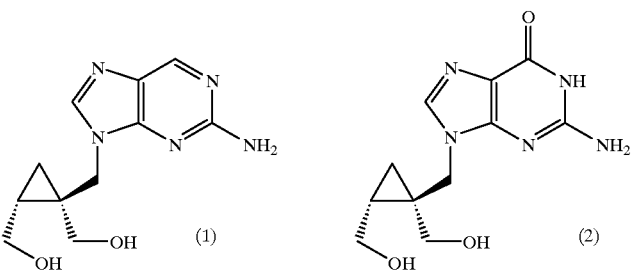

Namely, the present invention provides a process for purifying 2-amino-6-chloro-9-[(1'S,2'R)-1',2'-bis(hydroxymethyl)cyclopropane-1'-yl]methylpurine represented by the following formula (5), which comprises the step of selectively isolating 2-amino-6-chloro-9-[(1'S,2'R)-1', 2'-bis(hydroxymethyl)cyclopropane-1'-yl] methylpurine from a mixture of 2-amino-6-chloro-9-[(1'S,2'R)-1',2'-bis(hydroxymethyl) cyclopropane-1'-yl]methylpurine and 2-amino-6-chloro-7-[(1'S,2'R)-1',2'-bis (hydroxymethyl) cyclopropane-1'-yl]methylpurine represented by the following formula (6) by the crystallization:

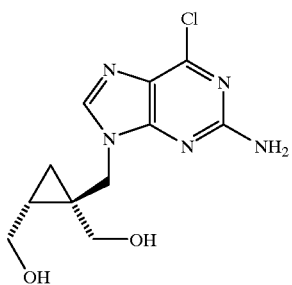

(5)

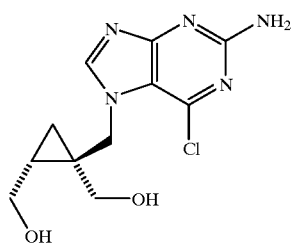

(6)

The purification can be efficiently conducted by using water or isopropyl alcohol as the solvent in the crystallization.

The present invention also provides 2-amino-6-chloro-9-[(1'S,2'R)-1', 2'-bis(hydroxymethyl)cyclopropane-1'-yl] methylpurine (5) represented by the following formula (5) which is an important intermediate for the preparation of 2-amino-9-[(1'S,2'R)-1',2'-bis(hydroxymethyl) cyclopropane-1'-yl]methylpurine (1) or 2-amino-9-[(1'S, 2'R)-1',2'-bis(hydroxymethyl)cyclopropane-1'-yl] methylguanine (2).

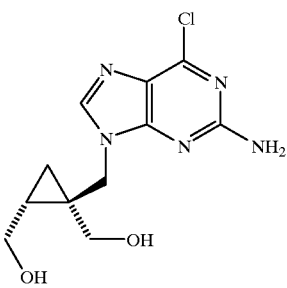

(5)

The present invention is also effective for the purification of a mixture of optical isomers of compounds (5) and (6). Namely, the present invention provides a process for purifying 2-amino-6-chloro-9-[(1'R,2'S)-1',2'-bis(hydroxymethyl) cyclopropane-1'-yl]methylpurine, which comprises the steps of selectively isolating 2- amino-6-chloro-9-[(1'R,2'S)-1',2'-bis(hydroxymethyl)cyclopropane-1'-yl]methylpurine from a mixture of 2-amino-6-chloro-9-[(1'R,2'S)-1',2'-bis(hydroxymethyl)cyclopropane-1'-yl]methylpurine and 2-amino-6-chloro-7-[(1'R,2'S)-1',2'-bis(hydroxymethyl) cyclopropane-1'-yl]methylpurine by the crystallization. Also in this process, the purification can be efficiently conducted by using water or isopropyl alcohol as the solvent.

DESCRIPTION OF THE PREFERRED EMBODIMENTS

The mixture of 2-amino-6-chloro-9-[(1'S,2'R)-1',2'-bis(hydroxymethyl) cyclopropane-1'-yl]methylpurine (5) and 2-amino-6-chloro-7-[(1'S,2'R)-1',2'-bis (hydroxymethyl) cyclopropane-1'-yl]methylpurine (6) is obtained by reducing lactone parts of a mixture of 2-amino-6-chloro-9-(3'-oxa-2'-oxobicyclo[3.1.0]hexane-1'-yl)methylpurine (3) and 2-amino-6-chloro-7-(3'-oxa-2'-oxobicydo[3.1.0]hexane-1'-yl)methylpurine (4), obtained by reacting 2-amino-6-chloropurine with a compound obtained by introducing a leaving group into a hydroxyl group of (3-oxa-2-oxobicydo[3.1.0]hexane-1-yl)methanol.

In particular, the intended mixture of 2-amino-6-chloro-9-[(1'S,2'R)-1',2'-bis(hydroxymethyl)cyclopropane-1'-yl]methylpurine (5) and 2-amino-6-chloro-7-[(1'S,2'R)-1',2'-bis(hydroxymethyl)cyclopropane-1'-yl]methylpurine (6) can be obtained by reacting 2-amino-6-chloropurine with a compound obtained by introducing a leaving group into a hydroxyl group of a (3-oxa-2-oxobicydo[3.1.0]hexane-1-yl)methanol such as (3-oxa-2-oxobicydo[3.1.0]hexane-1-yl)methylmethanesulfonate in the presence of a base such as potassium carbonate in a solvent such as N,N-dimethylformamide, removing insoluble matters such as potassium carbonate by the filtration, concentrating the filtrate, adding an excess amount of ethanol to the concentrate to precipitate crystals, thereby obtaining a mixture of the condensation product substituted at the N-9 position and that substituted at the N-7 position (J. P. KOKAI Nos. Hei 7-316155 and Hei 7-81732), isolating the mixture, suspending the mixture in a solvent such as ethanol or water, and adding a reducing agent such as sodium borohydride to conduct the reaction. The ratio of compound (5) to compound (6), which varies depending on the reaction conditions, is usually in the range of about 70:30 to 90:10.

When sodium borohydride is used as the reducing agent for the reduction reaction, the reaction is conducted at 10 to 40° C., preferably 30° C. under stirring overnight, and after the completion of the reaction, unreacted sodium borohydride is deactivated with an acid such as 6 mol/l aqueous hydrochloric acid solution, following by separation of the precipitate by the filtration, controlling pH of the filtrate at around neutral (pH: 6.0 to 7.0) with an alkali such as an aqueous sodium hydroxide solution, and concentrating the resulting solution to be used as material for the crystallization.

Then the intended compound (5) is obtained by dissolving the mixture of compounds (5) and (6) obtained as described above in water or isopropanol, cooling the obtained solution to separate the precipitated compound (5), and washing the obtained crystals.

The amount of water to be added as the solvent for the crystallization is such that the initial concentration of intended compound (5) will be 5 to 20% by weight, preferably 9 to 12% by weight, and that of isopropanol is such that the initial concentration of intended compound (5) will be 5 to 15% by weight, preferably 7 to 10% by weight. The quantity of compound (5) in the mixture of the starting compounds (5) and (6) can be determined according to the liquid chromatography. When the mixture is not dissolved even by adding the solvent for the crystallization, the mixture is heated to 60 to 80° C. which temperature varies depending on the ratio of compound (5) to compound (6).

Compound (5) is crystallized out of the solution, obtained by adding the solvent for the crystallization to the mixture of compounds (5) and (6), by slowly cooling the solution to crystallize intended compound (5) and once the crystals being precipitated out, further cooling the crystals to age them. For the efficient removal of compound (6), the cooling temperature is 3 to 8° C., preferably 4 to 7° C., because unnecessary compound (6) is also precipitated when the cooling temperature is excessively lowered.

The yield can be increased by stirring the reaction mixture at 25° C. or lower overnight before the crystals precipitate our. Seed crystals may be used for the crystallization.

By isolating the resultant crystals by an ordinary method such as filtration, 2-amino-6-chloro-9-[(1'S,2'R)-1',2'-bis(hydroxymethyl)cyclopropane-1'-yl]methylpurine (5) having a high purity can be obtained. The amount of the isomer in the N-7 position (6) is not larger than 1 area % as determined by HPLC analysis.

Since compound (5) is most efficiently purified by the selective crystallization from the mixture of compounds (5) and (6) when water is used as the solvent for the reduction reaction as will be described below, water is usable as the solvents (including reduction reaction solvent and crystallization solvent) in the whole process. Therefore, this process can be advantageously employed on an industrial scale.

Methanol cannot be used as the crystallization solvent because the recovery is seriously low in this case. n-Hexane or ether cannot be used either as the crystallization solvent because the solubility of compounds (5) and (6) is seriously low.

Although there is an idea of dividing the mixture of compounds (3) and (4) by the crystallization after the completion of the condensation reaction, the solubility of compound (3) in, for example, acetonitrile, is substantially the same as that of compound (4) and, therefore, the compound substituted at N-7 position cannot be completely removed by the crystallization.

An antiviral agent (1) can be synthesized by the hydrogenolysis (dehalogenation) of chlorine group at the 6-position of the intermediate (5) thus obtained, and another antiviral agent (2) can be obtained by the hydrolysis reaction of chlorine group at the 6-position.

The antiviral agent (1) is obtained by the hydrogenolysis of chlorine group of the intermediate (5) obtained as described above, to conduct the dechlorination.

For example, the hydrogenolysis can be conducted by using 5% palladium/carbon or 10% palladium/carbon (preferably 5% palladium/carbon) and hydrogen or a hydrogen source such as triethylamine formate and ammonium formate or preferably ammonium formate.

When the hydrogenolysis reaction is conducted by using hydrogen, a base such as triethylamine must be added to the reaction system. When no base is added, the reduction reaction of imidazole ring in the purine skeleton excessively proceeds.

The hydrogenolysis reaction can be conducted by, for example, dissolving compound (5) in methanol or ethanol solvent, adding a catalytic amount [preferably 2 molar % based on compound (5)] of 5% palladium/carbon, then adding 1 to 3 molar equivalents, preferably 1.1 to 1.3 molar equivalents [based on compound (5)1, of ammonium formate and stirring the resultant mixture under heating (preferably around 60° C.) to obtain compound (1).

The antiviral agent (2) can be obtained by hydrolyzing compound (5), obtained as described above, with an acid, preferably 6 mol/l aqueous hydrochloric acid solution or an alkali solution, preferably 1 mol/l aqueous sodium hydroxide solution.

In particular, the antiviral agent (2) can be obtained by, for example, adding compound (5) to 6 mol/l aqueous hydrochloric acid solution, stirring the obtained mixture under heating (preferably around 60° C.) to obtain the intended product and, after the completion of the reaction, concentrating the product, neutralizing it with sodium hydroxide to form crystals, and isolating the obtained crystals.

Although it is possible to employ another process wherein a mixture of compounds (3) and (4) is subjected to the hydrogenolysis to form a compound (7) substituted at the N-9 position and an isomer (8) at N-7 position, and then the lactone parts thereof are reduced to form the antiviral agent (2), this process cannot be employed for the production on an industrial scale because the isomer (8) at N-7 position cannot be completely removed from the intermediate compound (7) by the crystallization with water and an alcohol.

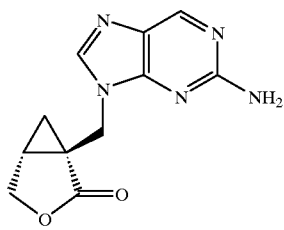

(7)

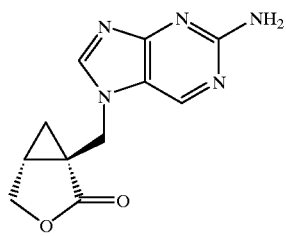

(8)

Further, although it is also possible to employ still another process wherein a mixture of compounds (3) and (4) is hydrolyzed to form a compound (9) substituted at the N-9 position and an isomer (8) at the N-7 position, and then the lactone parts thereof are reduced to form the antiviral agent (2), this process is disadvantageous for the production because the compounds (9) and (10) in the mixture cannot be separated by the crystallization.

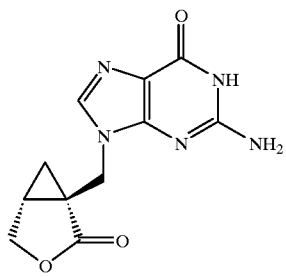

(9)

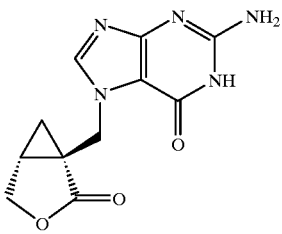

(10)

Thus, the preparation processes wherein the product is obtained through compounds (7) and (8) or through compounds (9) and (10) have a problem that since the compound substituted at the N-7 position is not completely removed, the final antiviral agent (1) or (2) is contaminated with a corresponding isomer at the N-7 position.

The present invention thus provides a process for preparing highly pure compound (5) usable as an intermediate for antiviral agents (1) and (2) on an industrial scale without necessitating a complicated column chromatographic operation.

EXAMPLES

The following Examples will further illustrate the present invention.

The liquid chromatographic analysis was conducted under the following conditions:
Column: YMC AM-302, 150×4.6 mm I.D.
Flow rate: 1.0 ml/min.
Eluents: A water(containing 0.1% TFA), B: 90% aqueous acetonitrile solution (containing 0.1% TFA) Gradient.

Example 1
Synthesis of 2-amino-6-chloro-9-(3'-oxa-2'-oxobicydo[3.1.0]hexane-1'-yl)methylpurine (3):

(Process 1) Process wherein N,N-dimethylformamide solution is used:

1.5 liters of a solution of 42.3 g (249.4 mmol) of 2-amino-6-chloropurine and 34.5 g (249.4 mmol) of potassium carbonate in N,N-dimethylformamide was stirred at 60° C. for one hour. 50.3 g (244.0 mmol) of (3-oxa-2-oxobicydo[3.1.0]hexane-1-yl]methylmethanesulfonate was added to the solution. Then the reaction temperature was elevated to 70° C. and the resultant mixture was stirred for 3 hours. Three hours after, the reaction mixture was completely cooled to room temperature. Insoluble solids were removed from the solution by the filtration. An N,N-dimethylformamide solution was distilled off from the filtrate with a vacuum pump to obtain a yellow syrup. 250 ml of 99.5% ethanol solution was added to the syrup, and the resultant mixture was violently stirred to obtain a slurry in which compounds (3) and (4) were precipitated in the form of a gum. Ethanol was distilled off from the slurry to obtain a syrup. 250 ml of 99.5% ethanol was added to the syrup and the resultant mixture was stirred at room temperature to obtain a slurry containing crystals of compounds (3) and (4). The crystals were separated, washed with 99.5% ethanol and dried by heating to obtain 55.62 g of a mixture of compounds (3) and (4) in the form a light yellow solid. Compound (3) content was 75% by weight, and compound (4) content was 14% by weight. The intended title compound (3) was thus obtained in a yield of 61%.

The physical properties of the obtained compound were the same as the data described in J. P. KOKAI No. Hei 7-316155.

(Process 2) Process wherein the reaction is carried out in acetonitrile solvent:

400 ml of a solution of 11.76 g (69.35 mmol) of 2-amino-6-chloropurine and 28.76 g (208.05 mmol) of potassium carbonate in acetonitrile was stirred in an oil bath at 70° C. for one hour. 14.3 g (69.35 mmol) of (3-oxa-2-oxobicydo[3.1.0]hexane-1-yl]methylmethanesulfonate was added to the solution. Then the reaction temperature was elevated to 80° C. and the resultant mixture was stirred for 4 hours under heating. Then the reaction liquid was completely cooled to room temperature. Insoluble solids were removed from the solution by the filtration to obtain 352 g of the filtrate [compound (3) content: 3.66% by weight]. Acetonitrile was distilled off until the amount of the filtrate was reduced to 35.94 g to concentrate the filtrate to form crystals. After the precipitation of the solid mixture of compound (3) and isomer (4) thereof at the N-7 position, the filtrate was stirred under cooling at 5° C. for 15 hours. After the filtration, 14.69 g of a mixture of compound (3) and by-product (4) was obtained [compound (3) content was 79% by weight, and compound (4) content was 19% by weight. The yield of intended compound (3) was 60%].

Example 2
Synthesis of 2-amino-6-chloro-9-[(1'S,2'R)-1',2'-bis(hydroxymethyl)cyclopropane-1'-yl]methylpurine (5):

(Process 1) Process wherein ethanol solvent is used:

59.0 g of a mixture of compound (3) and isomer (4) thereof at the N-7 position [compound (3) content: 178.9 mmol] was suspended in 1500 ml of 99.5% ethanol solution. The suspension was cooled to 5° C., and 15.6 g [2 molar equivalents based on compound (3)] of sodium borohydride was slowly added to the suspension. Then the reaction liquid was heated to 25° C. and stirred overnight. The disappearance of the starting materials was confirmed by HPLC [yield of compound (5) was 96%], and remaining sodium borohydride was decomposed by dropping 69.0 ml of 6 mol/l aqueous hydrochloric acid solution under cooling with an ice bath. The salt thus precipitated was separated, and the filtrate was neutralized with 2 mol/l aqueous sodium hydroxide solution (pH: 7.0±0.5) and concentrated by heating under reduced pressure until no more ethanol solvent had remained to obtain 75.68 g of a syrup. The syrup was dissolved in 350 ml of water by stirring under heating (50° C.) (crystallization concentration: 11% by weight). The obtained solution was stirred at room temperature overnight to continue the crystallization at 5° C. (the final mother liquor concentration: 3% by weight). The crystals were separated, washed with cold water (25 ml, 12 times) and dried by heating (50° C.) under reduced pressure to obtain 37.19 g of the intended product (content: 95% by weight, crystal recovery rate: 76%). The physical properties of the obtained compound coincided with data given in J. P. KOKAI No. Hei 5-78357. For reference, the analytical data are given below:

Appearance: white solid

1H-NMR (300 MHz, DMSO-d6): δ 0.44 ppm (t, J=5.4 Hz, 1H), 0.93 (dd, J=4.9, 8.6Hz, 1H), 1.32 (m, 1H), 3.29–3.44, 3.58–3.64 (m, 4H), 3.99 (d, J=14.1 Hz, 1H), 4.06 (d, J=14.0 Hz, 1H), 4.7 (bs, 2H), 6.88 (bs, 2H), 8.18 (s, 1H)

MS (ESI): 284.1 (MH+).

(Process 2) Process wherein water is used as the solvent:

5.0 ml of water was added to 230 mg of a mixture of compound (3) and isomer (4) thereof at the N-7 position to obtain a suspension. 74 mg of sodium borohydride was slowly added to the suspension at room temperature. The reaction liquid was stirred at room temperature overnight to obtain a reaction liquid containing the title compound (5) and its isomer (6) at the N-7 position. The reaction liquid was after-treated with 6 mol/l aqueous hydrochloric acid solution. After the neutralization, water was distilled until the crystallization conditions described in above process 1 were realized. After the crystallization, the title compound (5) was obtained.

Example 3
Synthesis of 2-amino-9-[(1'S,2'R)-1',2'-bis(hydroxymethyl)cyclopropane-1'-yl] methylpurine (1):

(Process 1) Process wherein ammonium formate is used:

2.67 g of ammonium formate was added to 100 ml of a solution of 10.0 g of compound (5) (content: 98.8% by weight) and 4.73 g of 5% palladium/carbon (wet, water content: 48%) in ethanol (99.5%). The mixture was stirred under heating in an oil bath at 80° C. After confirming the disappearance of starting material (5) by HPLC, the reaction liquid was cooled to a temperature around room temperature and then filtered through Celite. The filtrate was concentrated and dried to obtain 9.51 g (content: 82.7% by weight) of the title compound (1) in the form of a white solid (yield: 96%). The physical properties of the obtained compound coincided with data given in J. P. KOKAI No. Hei 5-78357. For reference, the analytical data are given below:

Appearance: white solid

1H-NMR (300 MHz, DMSO-d6): δ 0.43 ppm (t, J=5.2 Hz, 1H), 0.93 (dd, J=8.6, 4.9Hz, 1H), 1.30 (tt, J=8.5, 6.2Hz, 1H), 3.31 (dd, J=12.1, 4.7Hz, 1H), 3.35 (m, 1H), 3.42 (dd, J=12.1, 6.0Hz, 1H), 3.61 (dt, J=11.8,6.0Hz, 1H), 3.97 (d, J=14.1 Hz, 1H), 4.08 (d, J=14.0 Hz, 1H), 4.57 (t, J=5.3Hz, 1H, $D_2O$ exchangeable, —OH), 4.68 (dd, J=5.8, 4.8Hz, 1H, $D_2O$ exchangeable, —OH), 6.48 (br, 2H, $D_2O$ exchangeable, —NH), 8.11 (s, 1H), 8.57 (s, 1H) 13C-MNR (75 MHz, DMSO-d6): δ 14.0 ppm, 24.5,26.5, 47.3, 60.5, 60.7, 126.6, 142.7, 148.8, 153.3, 160.4

HRMS (FAB, DMSO-PEG): m/z 250.1294 (250.1304 calcd. for $C_{11}H_{16}N_5O_2$, M+H)

(Process 2) Process wherein hydrogen gas (triethylamine added) is used as hydrogen source:

153 mg of compound (5) was dissolved in 6 ml of methanol. Then 81 mg of 5% palladium/carbon [3 molar % based on compound (5), wet] and 0.074 ml of triethylamine were added to the solution, and the resultant mixture was stirred in hydrogen gas atmosphere at room temperature under atmospheric pressure for 26 hours. The 5% palladium/carbon was removed by the filtration through Celite. The filtrate was concentrated and dried to obtain the title compound (1) (yield: 94%). The physical properties of compound (1) thus obtained coincided with data given in J. P. KOKAI No. Hei 5-78357.

(Process 3) Process wherein triethylamine formate is used as hydrogen source:

150 mg of compound (5) was dissolved in 3 ml of methanol. 98 mg of 5% palladium/carbon [3 molar % based on compound (5), wet], 0.37 ml of triethylamine and 0.1 ml of formic acid were added to the solution, and the resultant mixture was stirred under heating at 60° C. in a bath. Two hours after, the 5% palladium/carbon was removed by the filtration through Celite. The filtrate was concentrated and dried to obtain the title compound (1) (yield: 94%). The physical properties of compound (1) thus obtained coincided with data given in J. P. KOKAI No. Hei 5-78357.

(Process 4) Synthesis of 9-[1'S,2'R]-1',2'-bis(hydroxymethyl)cyclopropane-1'-yl]methylguanine (2):

(Process 1) Hydrolysis with acidic aqueous solution:

0.97 g of compound (5) was added to 15 ml of 6 mol/l aqueous hydrochloric acid solution, and the obtained mixture was stirred under heating at 60° C. for 1.5 hours. The reaction liquid was concentrated to a volume of 4 ml and then neutralized with 6 mol/l aqueous sodium hydroxide solution to precipitate crystals. The liquid containing the crystals of the intended compound (2) was cooled to 5° C. and stirred overnight. After the filtration followed by washing with water, 0.78 g of the title compound (2) in the form of a white solid was obtained. The physical properties of compound (2) thus obtained coincided with data given in J. P. KOKAI No. Hei 6-80670.

(Process 2) Hydrolysis with aqueous alkali solution:

0.2 g of compound (5) was added to 10 ml of 1 mol/l aqueous sodium hydroxide solution and the resultant mixture was stirred under heating at 60° C. to obtain the intended compound (2). The physical properties of compound (2) thus obtained coincided with data given in J. P. KOKAI No. Hei 6-80670.

What is claimed is:

1. A process for separating 2-amino-6-chloro-9-[(1'S,2'R)-1',2'-bis(hydroxymethyl)-cyclopropane-1'-yl]methylpurine, represented by formula (5)

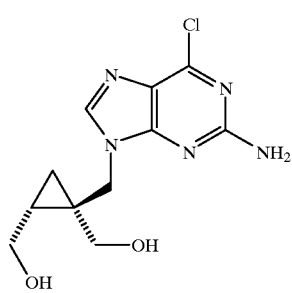

(5)

from a mixture of 2-amino-6-chloro-7-[(1'S,2'R)-1',2'-bis(hydroxymethyl)cyclopropane-1'-yl]methylpurine, represented by formula (6)

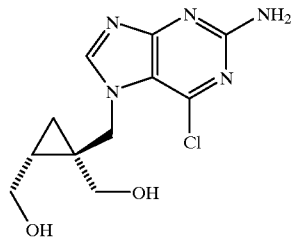

(6)

and 2-amino-6-chloro-9-[(1'S,2'R)-1',2'-bis(hydroxymethyl)cyclopropane-1'-yl]methylpurine, which process comprises crystallizing 2-amino-6-chloro-9-[(1'S,2'R)-1',2'-bis(hydroxymethyl)cyclopropane-1'-yl]methylpurine from a solvent containing 2-amino-6-chloro-7-[(1'S,2'R)-1',2'-bis(hydroxymethyl)cyclopropane-1'-yl]methylpurine and 2-amino-6-chloro-9-[(1'S,2'R)-1',2'-bis(hydroxymethyl)cyclopropane-1'-yl]methylpurine; and separating 2-amino-6-chloro-9-[(1'S,2'R)-1',2'-bis(hydroxymethyl)cyclopropane-1'-yl]methylpurine from 2-amino-6-chloro-7-[(1'S,2'R)-1',2'-bis(hydroxymethyl)cyclopropane-1'-yl]methylpurine.

2. The process of claim 1, wherein the solvent is water or isopropyl alcohol.

3. The process of claim 1, wherein the solvent is water.

4. The process of claim 3, wherein an initial concentration of 2-amino-6-chloro-9-[(1'S,2'R)-1',2'-bis(hydroxymethyl)cyclopropane-1'-yl]methylpurine in water is 9 to 12% by weight.

5. The process of claim 3, wherein crystallization is carried out by cooling the water from a temperature of 50° C. to a temperature of 5° C.

6. The process of claim 1, wherein the crystallization is concluded at a temperature of from 3 to 8° C.

7. A process for separating 2-amino-6-chloro-9-[(1'R,2'S)-1',2'-bis(hydroxymethyl)-cyclopropane-1'-yl]methylpurine from a mixture of 2-amino-6-chloro-7-[(1'R,2'S)-1',2'-bis(hydroxymethyl)cyclopropane-1'-yl]methylpurine and 2-amino-6-chloro-9-[(1'R,2'S)-1',2'-bis(hydroxymethyl)cyclopropane-1'-yl]methylpurine, which process comprises crystallizing 2-amino-6-chloro-9-[(1'R,2'S)-1',2'-bis(hydroxymethyl)cyclopropane-1'-yl]methylpurine from a solvent containing 2-amino-6-chloro-7-[(1'R,2'S)-1',2'-bis(hydroxymethyl)cyclopropane-1'-yl]methylpurine and 2-amino-6-chloro-9-[(1'R,2'S)-1',2'-bis(hydroxymethyl)cyclopropane-1'-yl]methylpurine; and separating 2-amino-6-chloro-9-[(1'R,2'S)-1',2'-bis(hydroxymethyl)-cyclopropane-1'-yl]methylpurine from 2-amino-6-chloro-7-[(1'R,2'S)-1',2'-bis(hydroxymethyl)cyclopropane-1'-yl]methylpurine.

8. The process of claim 7, wherein the solvent is water or isopropyl alcohol.

9. The process of claim 7, wherein the solvent is water.

10. The process of claim 9, wherein crystallization is carried out by cooling the water from a temperature of 50° C. to a temperature of 5° C.

* * * * *